(12) United States Patent
Perryman et al.

(10) Patent No.: US 11,439,832 B2
(45) Date of Patent: Sep. 13, 2022

(54) IMPLANTABLE ELECTRONIC DEVICES

(71) Applicant: Stimwave Technologies Incorporated, Pompano Beach, FL (US)

(72) Inventors: Laura Tyler Perryman, Pompano Beach, FL (US); Graham Patrick Greene, Miami Beach, FL (US); Benjamin Speck, Boca Raton, FL (US); Patrick Larson, Surfside, FL (US); Paul Lombard, Coral Springs, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 111 days.

(21) Appl. No.: 16/691,738

(22) Filed: Nov. 22, 2019

(65) Prior Publication Data
US 2020/0215333 A1    Jul. 9, 2020

Related U.S. Application Data

(60) Provisional application No. 62/790,119, filed on Jan. 9, 2019.

(51) Int. Cl.
*A61N 1/375* (2006.01)
*A61N 1/378* (2006.01)
(Continued)

(52) U.S. Cl.
CPC .............. *A61N 1/375* (2013.01); *A61N 1/05* (2013.01); *A61N 1/3787* (2013.01);
(Continued)

(58) Field of Classification Search
CPC ...... A61N 1/375; A61N 1/05; A61N 1/37205; A61N 1/3787; A61N 1/37229;
(Continued)

(56) References Cited

U.S. PATENT DOCUMENTS 7,856,707 B2 * 12/2010 Cole ........................ A61N 1/05
29/844
8,897,894 B1 * 11/2014 Orinski .............. B23K 37/0408
607/137

(Continued)

FOREIGN PATENT DOCUMENTS

WO    WO 2012/138782    10/2012
WO    WO 2013/019757     2/2013
(Continued)

OTHER PUBLICATIONS

PCT International Search Report and Written Opinion in International Appln. No. PCT/US2020/060578, dated Jan. 11, 2021, 8 pages.

*Primary Examiner* — Catherine M Voorhees
(74) *Attorney, Agent, or Firm* — Fish & Richardson P.C.

(57) ABSTRACT

An implantable electronic device includes a flexible circuit board, one or more circuit components attached to the flexible circuit board and configured to convert electrical energy into electrical pulses, and one or more electrodes attached to the flexible circuit board without cables connecting the electrodes to each other or to the flexible circuit board, the one or more electrodes configured to apply the electrical pulses to a tissue adjacent the implantable electronic device.

20 Claims, 10 Drawing Sheets

(51) Int. Cl.
  *H05K 1/11* (2006.01)
  *A61N 1/05* (2006.01)
  *A61N 1/372* (2006.01)
  *H05K 1/18* (2006.01)
  *H01Q 1/38* (2006.01)
  *H01Q 1/27* (2006.01)

(52) U.S. Cl.
  CPC ...... *A61N 1/37205* (2013.01); *A61N 1/37229* (2013.01); *H01Q 1/273* (2013.01); *H01Q 1/38* (2013.01); *H05K 1/118* (2013.01); *H05K 1/189* (2013.01); *H05K 2201/0939* (2013.01)

(58) Field of Classification Search
  CPC .................. H05K 1/189; H05K 1/118; H05K 2201/0939; H05K 2201/0311; H05K 2201/10098; H05K 2201/10265; H05K 1/165; H05K 2201/0154; H01Q 1/38; H01Q 1/273
  See application file for complete search history.

(56) References Cited

U.S. PATENT DOCUMENTS

| | | | |
|---|---|---|---|
| 9,220,897 B2 | 12/2015 | Perryman et al. | |
| 9,248,276 B2* | 2/2016 | Pianca | A61N 1/0534 |
| 9,789,314 B2 | 10/2017 | Perryman et al. | |
| 10,238,874 B2 | 3/2019 | Perryman et al. | |
| 10,245,436 B2 | 4/2019 | Perryman et al. | |
| 2006/0161204 A1 | 6/2006 | Colvin et al. | |
| 2010/0010565 A1 | 1/2010 | Lichtenstein et al. | |
| 2011/0130816 A1* | 6/2011 | Howard | H01R 43/00 607/116 |
| 2014/0031837 A1* | 1/2014 | Perryman | A61N 1/3787 606/129 |
| 2015/0366508 A1* | 12/2015 | Chou | A61B 5/6858 600/374 |
| 2016/0023003 A1 | 1/2016 | Perryman et al. | |
| 2016/0101287 A1 | 4/2016 | Perryman et al. | |
| 2016/0184597 A1* | 6/2016 | Andresen | A61N 1/37229 607/60 |
| 2017/0143959 A1 | 5/2017 | Boling et al. | |
| 2017/0165476 A1* | 6/2017 | Greenberg | A61N 1/0543 |
| 2018/0008821 A1* | 1/2018 | Gonzalez | H05K 3/0064 |
| 2018/0008828 A1 | 1/2018 | Perryman et al. | |
| 2018/0169406 A1 | 6/2018 | Shah et al. | |
| 2018/0289971 A1 | 10/2018 | Yeh et al. | |
| 2019/0143124 A1 | 5/2019 | Perryman et al. | |
| 2019/0247660 A1 | 8/2019 | Perryman et al. | |
| 2019/0282297 A1* | 9/2019 | Schultz | A61B 18/1492 |
| 2021/0170184 A1 | 6/2021 | Greene | |

FOREIGN PATENT DOCUMENTS

| | | |
|---|---|---|
| WO | WO 2013/025632 | 2/2013 |
| WO | WO 2013/040549 | 3/2013 |
| WO | WO 2012/103519 | 3/2014 |

* cited by examiner

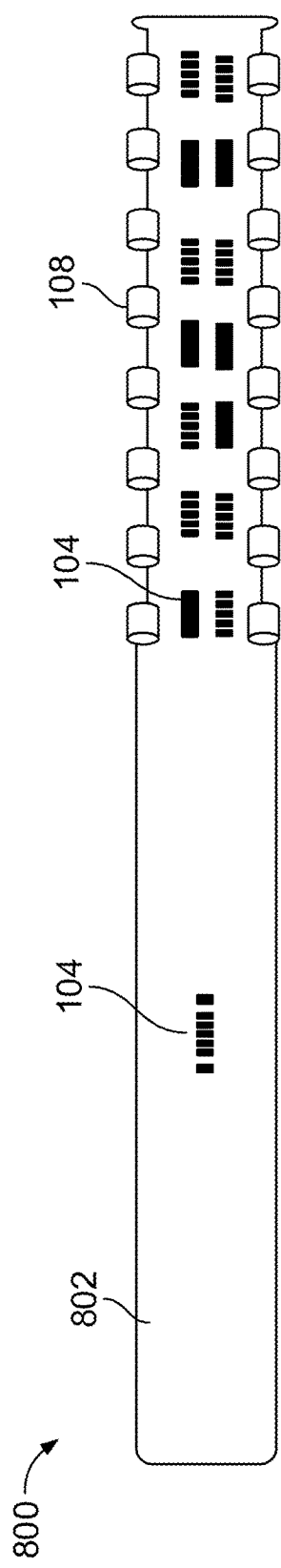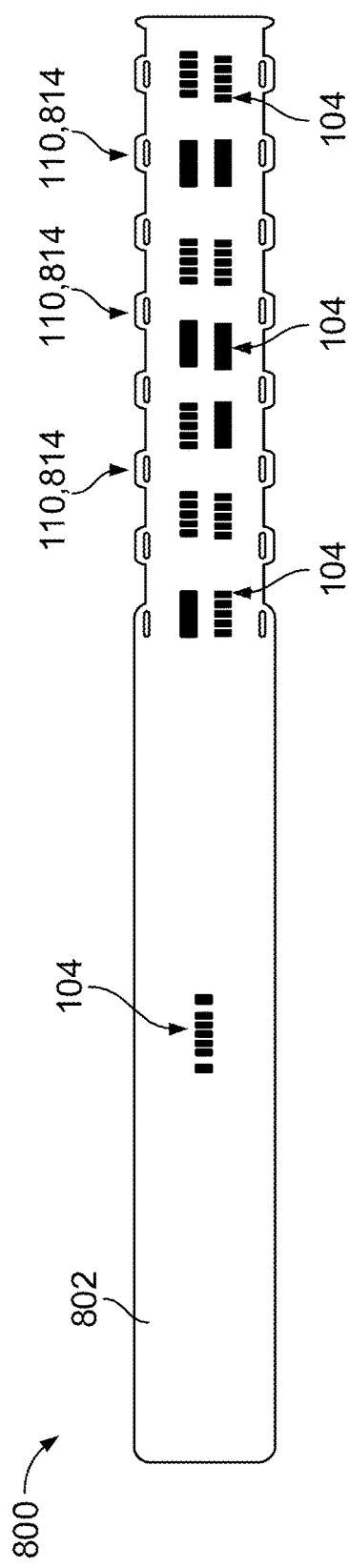

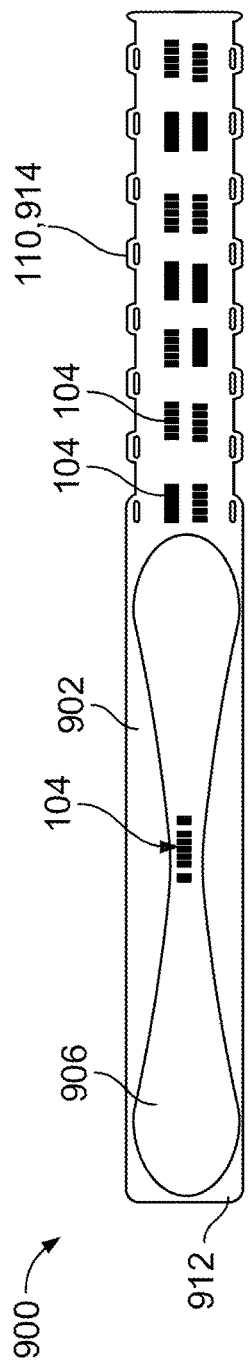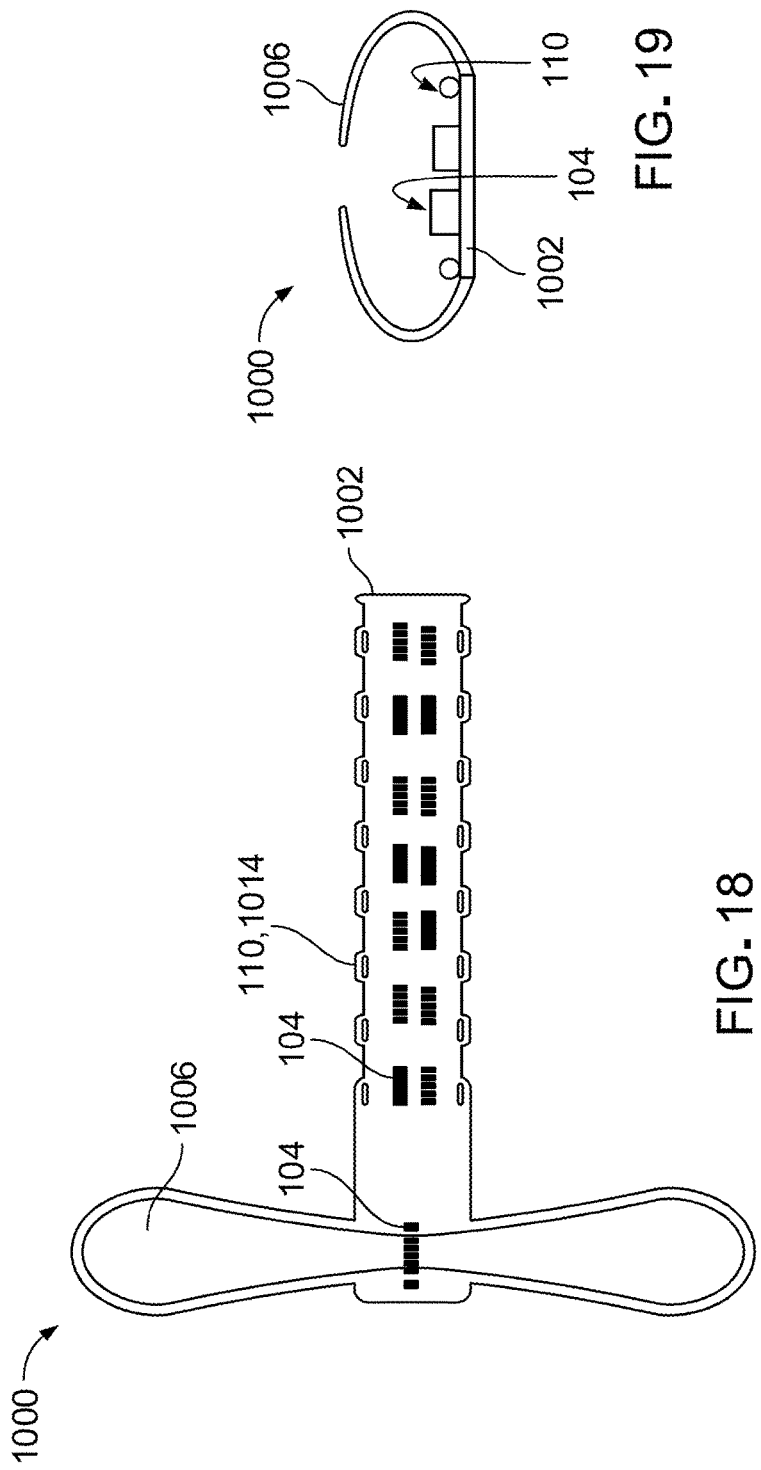

IMPLANTABLE ELECTRONIC DEVICES

CROSS-REFERENCE TO RELATED APPLICATION

This application claims the benefit of U.S. Provisional Application No. 62/790,119, filed Jan. 9, 2019, and titled "Implantable Electronic Devices," which is incorporated by reference.

TECHNICAL FIELD

This disclosure relates to monolithic electronic devices designed to be implanted within a patient's body for delivering electrical therapy to tissues within the body.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, electrodes on an implantable tissue stimulator can be used to pass pulsatile electrical currents of controllable frequency, pulse width, and amplitudes to a tissue. In many cases, such electrodes can experience mechanical failure at cables that connect the electrodes to each other and to an adjacent circuit board. The cables can render the tissue stimulator unsuitably stiff and, in some examples, the cables may pop off of the electrodes, break, fray, kink, or otherwise fail mechanically.

SUMMARY

In general, this disclosure relates to monolithic electronic devices designed to be implanted within a patient's body for delivering electrical therapy to tissues within the body. Such electronic devices include multiple electronic components secured to one small, flat substrate that can be delivered to the body through an introducer needle.

In one aspect, an implantable electronic device includes a flexible circuit board, one or more circuit components attached to the flexible circuit board and configured to convert electrical energy into electrical pulses, and one or more electrodes attached to the flexible circuit board without cables connecting the electrodes to each other or to the flexible circuit board, the one or more electrodes configured to apply the electrical pulses to a tissue adjacent the implantable electronic device.

Embodiments may provide one or more of the following features.

In some embodiments, the implantable electronic device further includes one or more joints at which the one or more electrodes are respectively attached to the flexible circuit board.

In some embodiments, the one or more joints include one or more of stainless steel, platinum, platinum-iridium, gallium-nitride, titanium-nitride, and iridium-oxide.

In some embodiments, the one or more joints are part of the one or more electrodes.

In some embodiments, the one or more joints have a thickness of about 0.05 mm to about 0.5 mm.

In some embodiments, the one or more electrodes are attached to the flexible circuit board respectively along one or more interior surfaces of the one or more electrodes.

In some embodiments, the one or more interior surfaces have a shape that is complimentary to at least one or more portions of the one or more joints.

In some embodiments, the one or more electrodes are attached to the flexible circuit board respectively along one or more exterior surfaces of the one or more electrodes.

In some embodiments, the one or more exterior surfaces have a shape that is complimentary to at least one or more portions of the one or more joints.

In some embodiments, the one or more electrodes are attached to the flexible circuit board in an automated manner.

In some embodiments, the one or more electrodes are attached to the flexible circuit board via laser welding, soldering, or conductive epoxy application.

In some embodiments, the one or more electrodes have a generally tubular shape.

In some embodiments, the one or more electrodes are directly attached to the flexible circuit board.

In some embodiments, the one or more electrodes are attached to the flexible circuit board within a compressive mechanical structure.

In some embodiments, the implantable electronic device further includes an antenna attached to the flexible circuit board and configured to receive an input signal carrying the electrical energy.

In some embodiments, the antenna includes a layer of the flexible circuit board.

In some embodiments, the antenna is oriented parallel to the one or more circuits.

In some embodiments, the antenna is oriented perpendicular to the one or more circuits.

In some embodiments, the antenna includes two separate portions.

In some embodiments, the implantable electronic device is sized to be passed through an introducer needle.

DESCRIPTION OF DRAWINGS

FIG. 14 is a top view of an electronic device.

FIG. 15 is a top view of the electronic device of FIG. 14, with electrodes omitted for illustration of underlying components.

FIG. 16 is a side view of the electronic device of FIG. 14, with electrodes omitted for illustration of underlying components.

FIG. 17 is a top view of an electronic device including an antenna oriented parallel to circuit components of the electronic device.

FIG. 18 is a top view of an electronic device including an antenna oriented perpendicular to circuit components of the electronic device.

FIG. 19 is a side view of the electronic device of FIG. 18.

DETAILED DESCRIPTION

Figure 1:
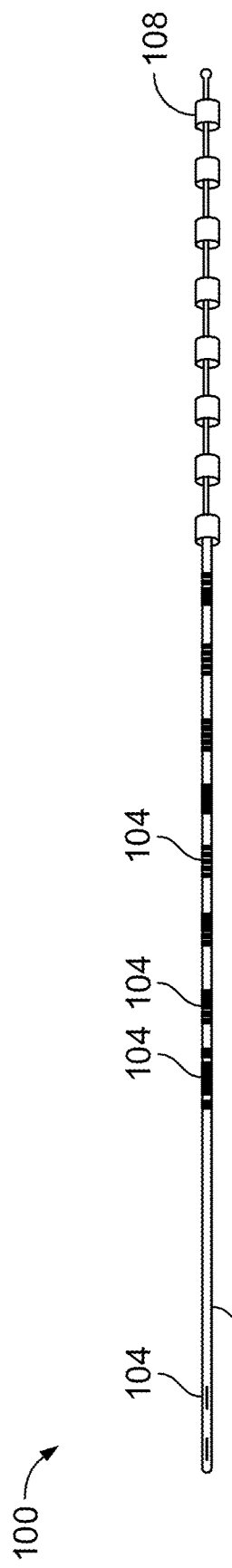
FIG. 1 is a top view of an electronic device.
Figure 2:
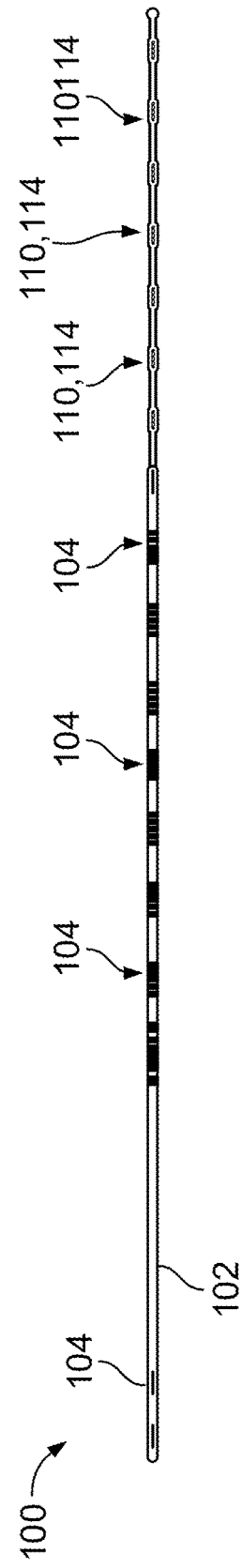
FIG. 2 is a top view of the electronic device of FIG. 1, with electrodes omitted for illustration of underlying components.
Figure 3:
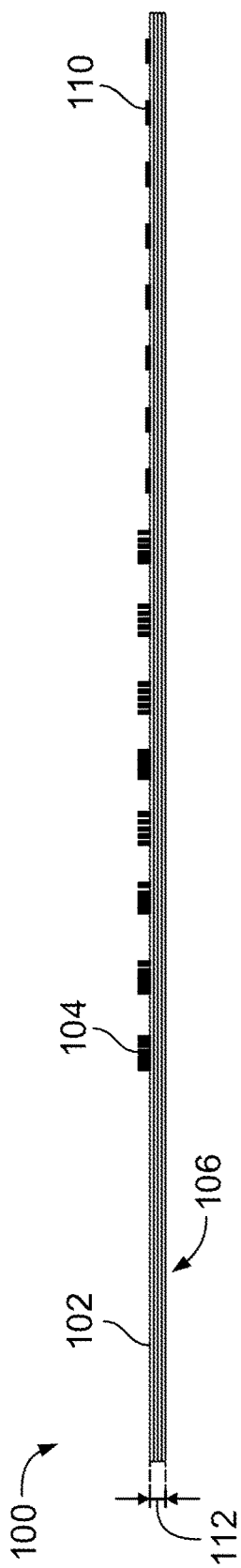
FIG. 3 is a side view of the electronic device of FIG. 1, with electrodes omitted for illustration of underlying components.

FIGS. 1-3 illustrate various views of an electronic device 100 designed to be implanted within a patient's body for delivering electrical therapy to tissues within the body. For example, the electronic device 100 may be provided within a housing of a tissue stimulator or connected to a tissue stimulator. The electronic device 100 is a monolithic device for which electronic components are secured to one small, flat substrate that can be delivered to the body through an introducer needle. The electronic device 100 includes a circuit board 102 and various circuit components 104, an antenna 106, and electrodes 108 that are secured to the circuit board 102. The electronic device 100 further includes multiple pads 110 at which the electrodes 108 are respectively attached to the circuit board 102.

The circuit board 102 is a flexible substrate including multiple layers 112 in which the antenna 106 is interposed. The circuit board 102 defines contact sites 114 that locate the pads 110 and typically has a length of about 0.5 mm to about 4 mm, a width of about 0.05 mm to about 0.5 mm, and a thickness of about 0.0125 mm to about 0.5 mm. The circuit board 102 is typically made of a dielectric substrate, such as polyimide. In some embodiments, additional dielectric materials may be applied to the circuit board 102 along certain regions for stiffening.

The circuit components 104 are distributed along the length of the circuit board 102 and may be secured to the circuit board 102 via solder, solder paste, or conductive epoxy. Example circuit components 104 include diodes, capacitors, resistors, semiconductors, and other electromechanical components. The antenna 106 is integrated directly into one of the layers 112 of the circuit board and is designed to receive an input signal carrying electrical energy that can be used by the circuit components 104 and relayed to the electrodes 108 so that the electrodes 108 can apply one or more electrical pulses to adjacent tissue. Arrangement of the antenna 106 along a layer 112 contributes to a compact and simplified structure of the electronic device 100 in that such configuration avoids the need for additional cables or attachment features to communicate the antenna 106 with the circuit components 104. In some embodiments, the electronic device 100 may include additional trace pathways to serialize the circuit components 104 and render the electronic device 100 viewable with standard imaging equipment (e.g., X-ray equipment).

The electrodes 108 are embodied as generally cylindrical structures that can be secured to the pads 110 at the contact sites 114. The electrodes 108 typically have a length of about 0.5 mm to about 6 mm and an internal diameter of about 0.9 mm to about 1.5 mm.

Figure 4:
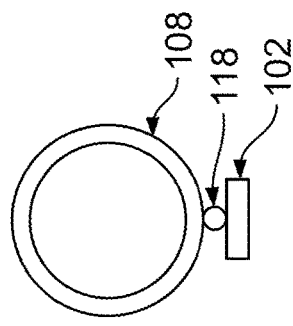
FIG. 4 is a side cross-sectional view of the electronic device of FIG. 1, with a circuit board attached to electrodes along interior surfaces of the electrodes.

Referring to FIG. 4, the electrodes 108 are attached to the contact sites 114 and around the circuit board 102 at joints 118 that extend along axes 120 of the electrodes 108. The joints 118 provide additional surface area at which the electrodes 108 can be attached to the circuit board 102. The electrodes 108 and the joints 118 are typically made of one or more materials, such as stainless steel, platinum, platinum-iridium, gallium-nitride, titanium-nitride, iridium-oxide, or other materials. The joints 118 have a circular cross-sectional shape that provides an outer surface at which the electrodes 108 can be sufficiently attached in extent. In some embodiments, the joints 118 are attached to the circuit board 102 at the contact sites 114 in an automatic manner via surface mount techniques that utilize tape and reel machine mechanisms or soldered by hand. The joints 118 typically have a thickness of about 0.05 mm to about 0.5 mm and typically have a length that is a bit shorter than the respective electrodes 108.

Figure 5:
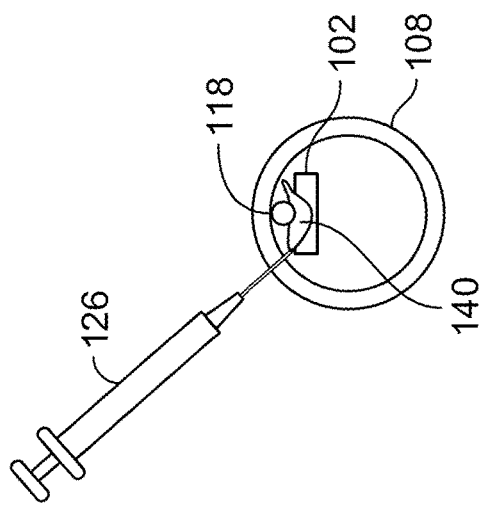
FIG. 5 illustrates various techniques by which the electrodes of the electronic device of FIG. 1 can be attached to the flexible circuit board of the electronic device, including laser welding, soldering, and conductive epoxy application.
Figure 7:
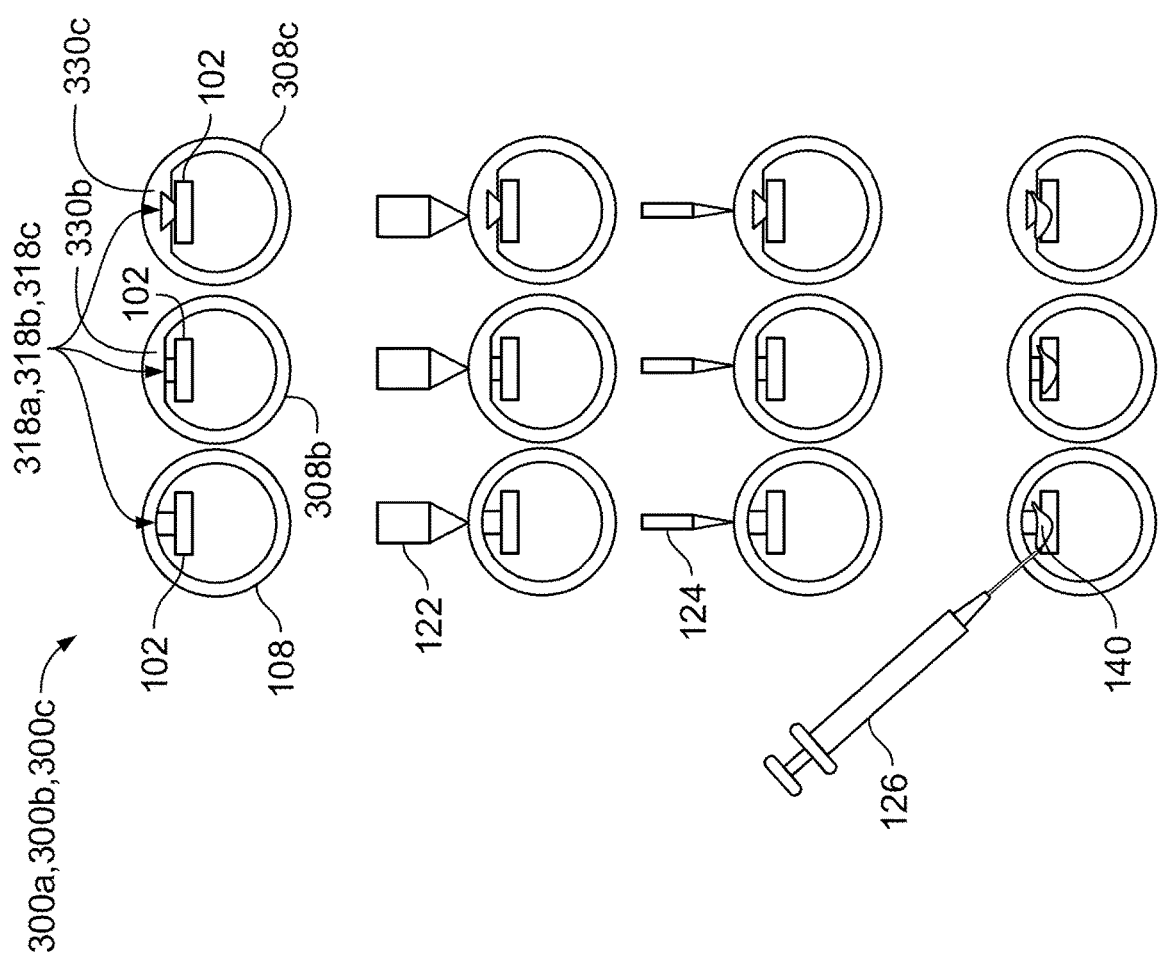

Referring to FIG. 5, the electrodes 108 may then be attached to the circuit board at the joints 118 using various attachment techniques, such as laser welding, soldering, and conductive epoxy application (e.g., chemical bonding). Such techniques can be carried out automatically using computer controlled processing heads (e.g., laser heads 122, soldering tips 124, and syringes 126 applying epoxy 140) that can be controlled to attach multiple electrodes 108 to the joints 118 on the circuit board 102 in one pass or in multiple passes. In this manner, the electrodes 108 can be attached to the circuit board 102 in a uniform manner within specified tolerances and without cables (e.g., stainless steel wires, braided wires, or other wires) extending along the circuit board 102 and between the electrodes 108 that would otherwise need to be manually assembled with the electrodes 108 and the circuit board 102. As compared to conventional implantable electronic devices for which electrodes are secured to a circuit board via multiple cables, the electronic device 100 is more easily assembled (e.g., automatically and more quickly at a lower cost), more flexible, can withstand more bending forces (e.g., avoiding the problem of cables popping off of electrodes), is more mechanically robust within a moving body, and is therefore less likely to fail mechanically. Additionally, the electrodes 108 are assembled more uniformly with respect to positional accuracy and mechanical integrity, as compared to electrodes that are manually secured to a circuit board with multiple cables.

Figure 6:
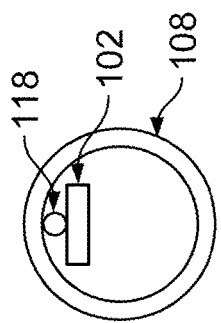
FIG. 6 is a side cross-sectional view of an electronic device, with a circuit board attached to electrodes along exterior surfaces of the electrodes.

In some embodiments, an overall footprint and three-dimensional shape of the electronic device 100 are selected to provide optimized electrical and mechanical performance of the circuit components 104 and the electrodes 108, provide minimal tissue contacting surface areas, and provide an anchoring structure that prevents or reduces movement of the electronic device 100 within the body. In some embodiments, While the electronic device 100 has been described and illustrated as including certain dimensions, sizes, shapes, materials, arrangements, and configurations, in some embodiments, electronic devices that are similar in structure and function to the electronic device 100 may include different dimensions, sizes, shapes, materials, arrangements, or configurations. For example, FIG. 6 illustrates an electronic device 1500 that is similar in structure and function to the electronic device 100, except that the circuit board 102 is attached to the electrodes 108 along outside surfaces of the electrodes 108. In some embodiments, separate connection to the electrodes 108 can advantageously offer a wider variety of options for the form factor of the electrodes 108 or advantageously allow interfacing with previously placed electrodes that have a connector end that can be mated to a header connector. A connector header can allow for the electrode connectors to mate to the circuitry elements as a separate piece.

Figure 7:
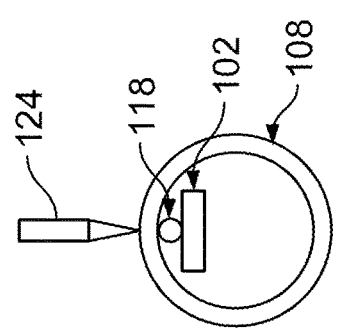
FIG. 7 illustrates side cross-sectional views of electronic devices including joints with non-circular cross-sectional shapes and with a circuit board attached to electrodes along interior surfaces of the electrodes.

While the electronic devices 100, 1500 have been described and illustrated as including cylindrical electrodes 118 and circular joints 118, in some embodiments, electronic devices that are similar in structure and function to either of the electronic devices 100, 1500 may include electrodes and joints that have different shapes or surface profiles. For example, as illustrated in FIG. 7, electronic devices 300a, 300b, 300c include joints 318a, 318b, 318c with non-circular (e.g., generally rectangular or trapezoidal) cross-sectional shapes. While the electronic device 300a includes the electrodes 108 that are formed to be adequately attached to the joint 318a, the electronic devices 300b, 300c include electrodes 308b, 308c that have non-circular interior cross-sectional shapes with thickened wall sections 330b, 330c that are formed to complement the joints 318b, 318c. In particular, the wall section 330b provides a flat interior surface for mating with the thin, rectangular joint 318b, and the wall section 330c provides a recessed cutout for mating with the trapezoidal joint 318c. As shown in FIG. 7, the electrodes 308b, 308c can also be attached to the circuit board 102 via various attachment techniques, such as laser welding, soldering, and conductive epoxy application, as discussed above with respect to the electronic device 100.

Figure 8:
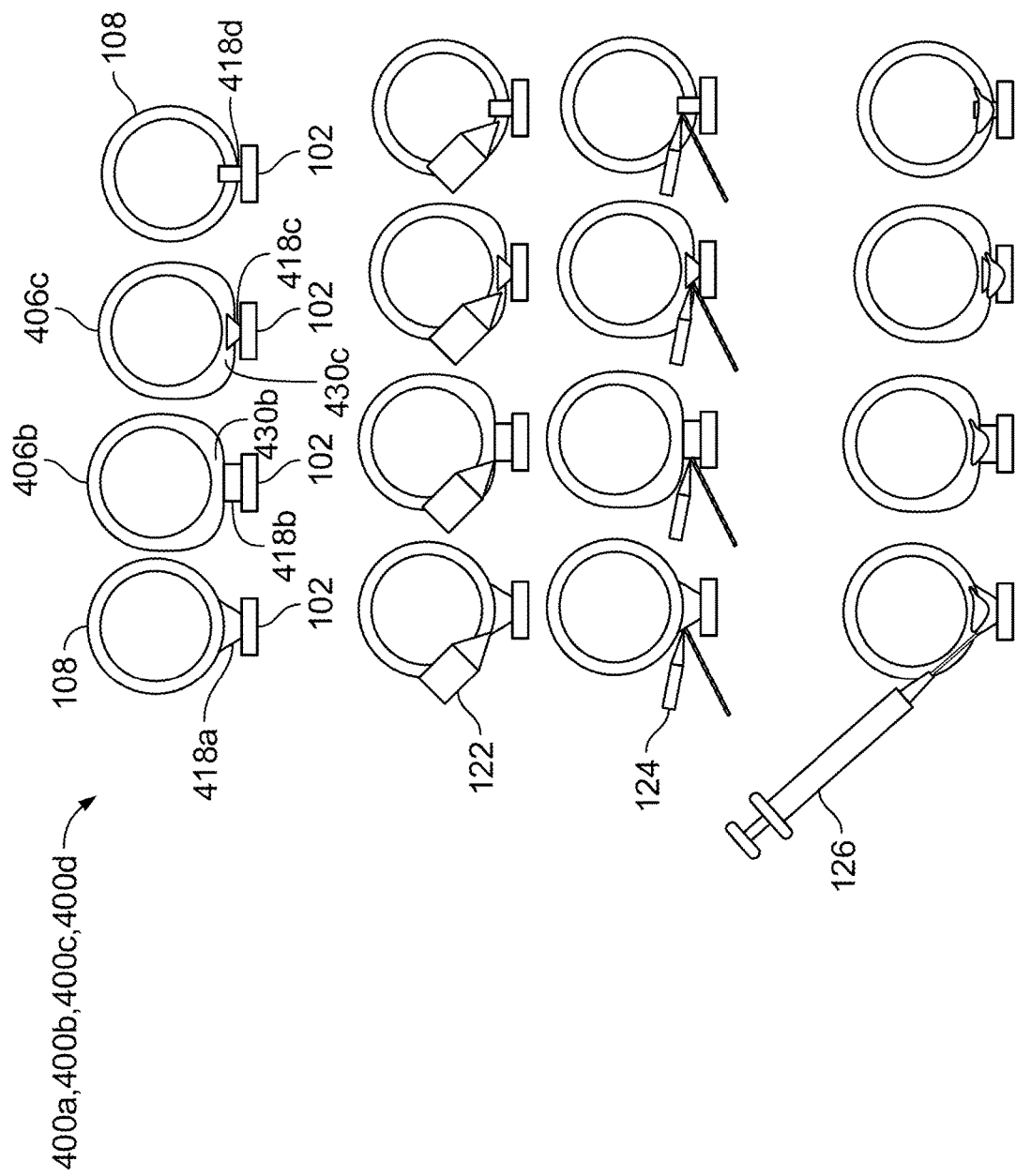
FIG. 8 illustrates side cross-sectional views of electronic devices including joints with non-circular cross-sectional shapes and with a circuit board attached to electrodes along exterior surfaces of the electrodes.

FIG. 8 illustrates electronic devices 400a, 400b, 400c, 400d for which electrodes are secured to the circuit board 102 along one side of the circuit board 102 such that the circuit board 102 is positioned external to the electrodes. The electronic devices 400a, 400b, 400c, 400d include joints 418a, 418b, 418c, 418d with non-circular (e.g., generally rectangular, trapezoidal, and other) cross-sectional shapes. While the electronic devices 400a, 400d include the electrodes 108 that are formed to be adequately attached to the joint 418a, 418d, the electronic devices 400b, 400c include electrodes 406b, 406c with non-circular exterior cross-sectional shapes with thickened wall sections 430b, 430c that are formed to complement the joints 418b, 418c. In particular, the wall section 430b provides a flat interior surface for mating with the rectangular joint 418b, and the wall section 430c provides a recessed cutout for mating with the trapezoidal joint 418c. As shown in FIG. 8, the electrodes 406b, 406c can also be attached to the circuit board 102 via various attachment techniques, such as laser welding, soldering, and conductive epoxy application, as discussed above with respect to the electronic devices 100, 1500.

Figure 9:
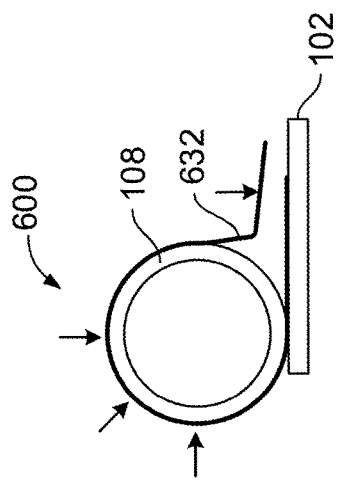
FIG. 9 is a side cross-sectional view of an electronic device that includes electrodes secured to a circuit board with a compressive mechanical structure.
Figure 10:
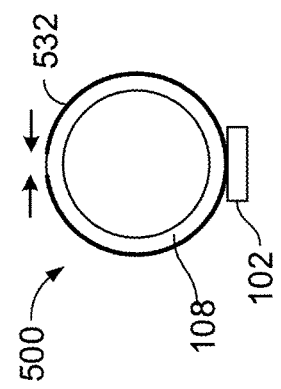
FIG. 10 is a side cross-sectional view of an electronic device that includes electrodes secured to a circuit board with a compressive mechanical structure.
Figure 11:
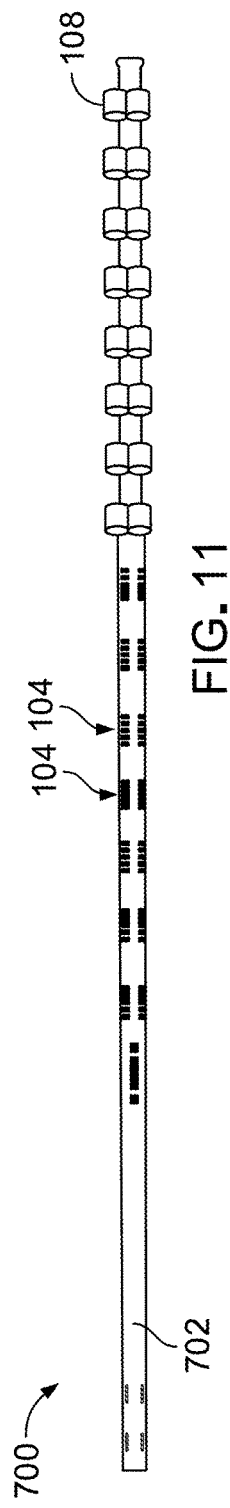
FIG. 11 is a top view of an electronic device.
Figure 12:
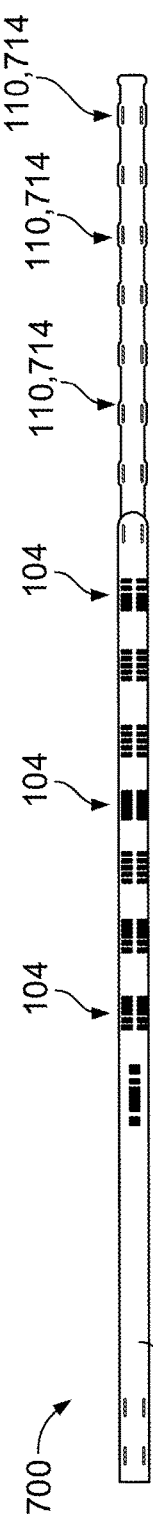
FIG. 12 is a top view of the electronic device of FIG. 11, with electrodes omitted for illustration of underlying components.
Figure 13:
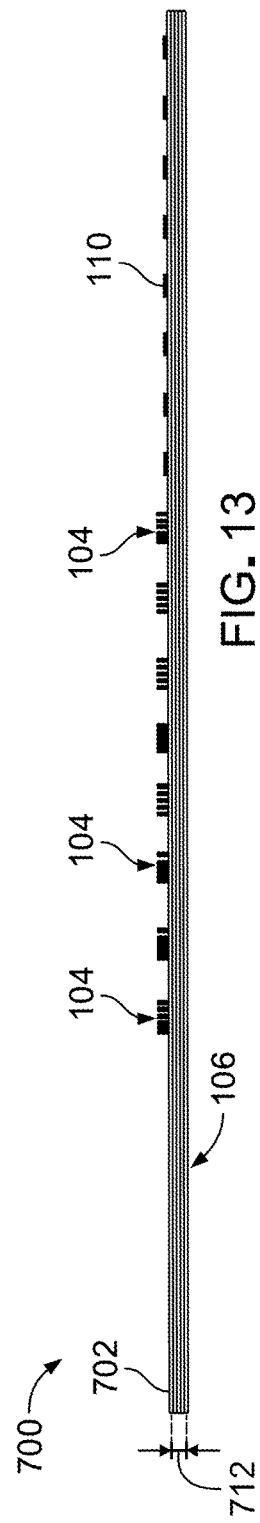
FIG. 13 is a side view of the electronic device of FIG. 11, with electrodes omitted for illustration of underlying components.

While the electronic devices 100, 300, 400, 1500 have been described and illustrated with electrode attachment to a circuit board using laser welding, soldering, or conductive epoxy application, in some embodiments, electronic devices that are substantially similar in construction and function to the any of electronic devices 100, 300, 400, 1500 may include electrodes that are attached via other techniques, such as welding, brazing, crimping, press fitting, swaging, or mechanical locking. For example, FIGS. 9 and 10 illustrate electronic devices 500, 600 for which the electrodes 108 are secured to the circuit board 102 within snap rings 532, 632 that are themselves attached to the circuit board 102 using standard surface mount pick and place with a reel of components, or soldered by hand.

While the electronic devices 100, 300, 400, 500, 600, 1500 have been described and illustrated with electrode attachment to a circuit board via the joints 118, 318, 418 and snap rings 532, 632, in some embodiments, electronic devices that are otherwise similar in construction and function to the any of electronic devices 100, 300, 400, 500, 600, 1500 may include electrodes that are attached directly to a circuit board using any of the above-mentioned techniques without such joints. In some embodiments, a joint may be integrated directly within such electrodes.

While the electronic device 100 has been illustrated with a single row of circuit components 104 and electrodes 108, in some embodiments, electronic devices that are similar in construction and function to the electronic device 100 may include more than one row of circuit components 104 and electrodes 108 or a different arrangement of circuit components 104 and electrodes 108. For example, FIGS. 11-16 illustrate electronic devices 700, 800 that have different arrangements of circuit components 104 and electrodes 108. The electronic devices 700, 800 are otherwise similar in structure and function to the electronic device 100 and accordingly further include circuit boards 702, 802, layers 712, 812, contact sites 714, 814, antennas 706, 806, and the pads 110. In the example electronic device 800, the wider circuit board 102 allows for a larger antenna structure.

FIG. 17 illustrates an electronic device 900 that is substantially similar in structure and function to the electronic device 800, except that the electronic device 900 includes an antenna 906 along a top layer 912 of a circuit board 902. The circuit board 902 includes contact sites 914. For such configuration in which the antenna 906 is oriented parallel to the circuit components 104, the circuit components 104 compete with the antenna 906 for an incident polarized transmission signal.

In some embodiments, an electronic device that is otherwise similar in construction and function to the electronic device 900 may include an antenna that is oriented perpendicular to circuit components 104. For example, FIG. 18 illustrates an electronic device 1000 that includes such an antenna 1006 disposed atop a circuit board 1002. The circuit board 1002 includes contact sites 1014. Accordingly, the circuit components 104 do not compete with the antenna 1006 for an incident polarized transmission signal, which is oriented perpendicular to the circuit components 104. In some embodiments, the antenna 1006 may be coiled upon itself to reduce a footprint of the electronic device 1000, as illustrated in FIG. 19. Such configurations may be introduced into the body in ways other than through an introducer needle.

Figure 20:
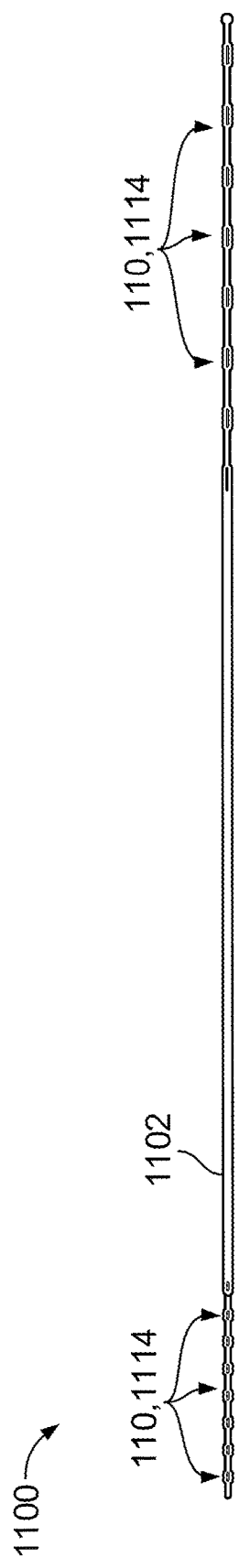
FIG. 20 is a top view of an electronic device including electrode contact sites positioned on both ends of a circuit board.

In some embodiments, an electronic device that is otherwise similar in construction and function to any of the above-discussed electronic devices may include electrodes that are positioned on both ends of a circuit board. For example, FIG. 20 illustrates a circuit board 1102 of a circuit board 1100 that includes contact sites 1114 for electrodes on both ends of the circuit board 1102. Though other components have been omitted for illustration, the electronic device 1100 may otherwise be similar in construction and function to the electronic device 100.

Figure 21:
FIG. 21 is a top view of an electronic device including an antenna formed from two separate portions.
Figure 22:
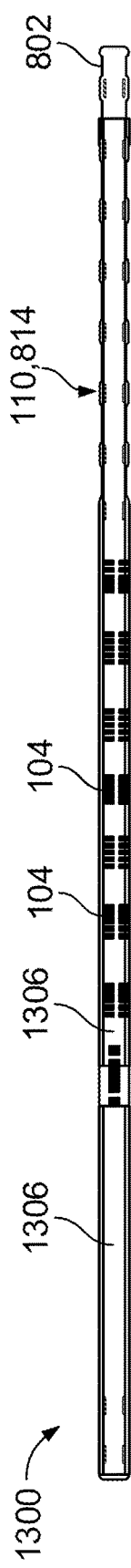
FIG. 22 is a top view of an electronic device including an antenna formed from two separate portions.

In some embodiments, an electronic device that is otherwise similar in construction and function to any of the above-discussed electronic devices may include an antenna that is made up of multiple portions. For example, FIGS. 21 and 22 illustrate electronic devices 1200, 1300 that include antennas 1206, 1306 that are formed of two portions along top layers of circuit boards 102, 802. Though other components have been omitted for illustration, the electronic devices 1200, 1300 may otherwise be similar in construction and function to the electronic devices 100, 800.

In some embodiments, an electronic device that is otherwise similar in construction and function to any of the above-discussed electronic devices may not include an embedded antenna.

In some embodiments, an electronic device that is otherwise similar in construction and function to any of the above-discussed electronic devices may include exposed and plated traces instead of electrodes.

Figure 23:
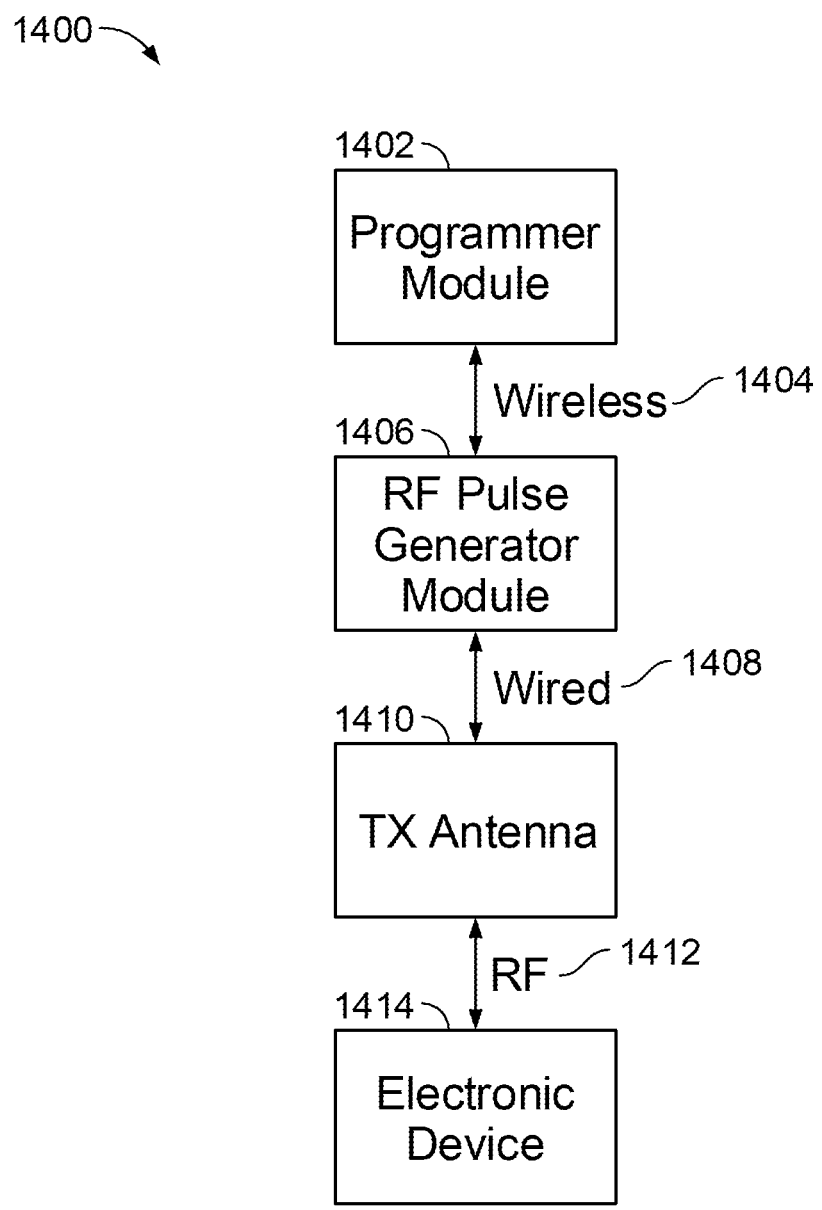
FIG. 23 is a system block diagram of a tissue stimulator system including the electronic device of FIG. 1.

In some embodiments, any of the above-discussed electronic devices may be provided as part of a tissue stimulation system, such as a neural stimulation system 1400, shown in FIG. 23. The neural stimulation system 1400 may be used to send electrical stimulation to targeted nerve tissue by using remote radio frequency (RF) energy without cables and without inductive coupling to power the electronic device 100, provided as a passive stimulator. In some examples, the targeted nerve tissues may be in the spinal column and include the spinothalamic tracts, dorsal horn, dorsal root ganglia, dorsal roots, dorsal column fibers, and peripheral nerves bundles leaving the dorsal column or brainstem, as well as any cranial nerves, abdominal, thoracic, or trigeminal ganglia nerves, nerve bundles of the cerebral cortex, deep brain and any sensory or motor nerves.

The neural stimulation system 1400 may include a controller module (e.g., an RF pulse generator module) and the passive electronic device 100, which includes one or more dipole antennas 106, circuit components 104, and electrodes 108 that can contact targeted neural tissue to provide tissue stimulation. The RF pulse generator module may include an antenna and may be configured to transfer energy from the module antenna to the implanted antennas. The circuit components 104 may be configured to generate electrical pulses suitable for neural stimulation using the transferred energy and to supply the electrical pulses to the electrodes 108 so that the pulses are applied to the neural tissue. For instance, the circuit components 104 may include wave conditioning circuitry that rectifies the received RF signal (for example, using a diode rectifier), transforms the RF energy to a low frequency signal suitable for the stimulation of neural tissue, and presents the resulting waveform to an electrode array. The circuit components 104 may also include circuitry for communicating information back to the RF pulse generator module to facilitate a feedback control mechanism for stimulation parameter control. For example, the electronic device 100 may send to the RF pulse generator module a stimulus feedback signal that is indicative of parameters of the electrical pulses, and the RF pulse generator module may employ the stimulus feedback signal to adjust parameters of the signal sent to the neural stimulator.

Still referring to FIG. 23, neural stimulation system 1400 includes a programmer module 1402, an RF pulse generator module 1406, a transmit (TX) antenna 1410 (e.g., a patch antenna, slot antenna, or a dipole antenna), and the electronic device 100. The programmer module 1402 may be a computer device, such as a smart phone, running a software application that supports a wireless connection 1404, such as Bluetooth.RTM. The application can enable the user to view the system status and diagnostics, change various parameters, increase/decrease the desired stimulus amplitude of the electrode pulses, and adjust feedback sensitivity of the RF pulse generator module 1406, among other functions.

The RF pulse generator module 1406 may include communication electronics that support the wireless connection 1404, the stimulation circuitry, and the battery to power the generator electronics. In some implementations, the RF pulse generator module 1406 includes the TX antenna embedded into its packaging form factor while, in other implementations, the TX antenna is connected to the RF pulse generator module 1406 through a wired connection 1408 or a wireless connection (not shown). The TX antenna 1410 may be coupled directly to tissue to create an electric field that powers the electronic device 100. The TX antenna 1410 communicates with the implanted electronic device 100 through an RF interface. For instance, the TX antenna 1410 radiates an RF transmission signal that is modulated and encoded by the RF pulse generator module 1410. The electronic device 100 contains one or more antennas 106, such as dipole antenna(s), to receive and transmit through RF interface 1412. In particular, the coupling mechanism between antenna 1410 and the one or more antennas 106 on the electronic device 100 is electrical radiative coupling and not inductive coupling. In other words, the coupling is through an electric field rather than a magnetic field.

Through this electrical radiative coupling, the TX antenna 1410 can provide an input signal to the implanted electronic device 100. This input signal contains energy and may contain information encoding stimulus waveforms to be applied at the electrodes 108 of the electronic device 100. In some implementations, the power level of this input signal directly determines an applied amplitude (for example, power, current, or voltage) of the one or more electrical pulses created using the electrical energy contained in the input signal. Within the implanted electronic device 100 are the circuit components 104 for demodulating the RF transmission signal, and the electrodes 108 to deliver the stimulation to surrounding neuronal tissue.

The RF pulse generator module 1406 can be implanted subcutaneously, or it can be worn external to the body. When external to the body, the RF generator module 1406 can be incorporated into a belt or harness design to allow for electric radiative coupling through the skin and underlying tissue to transfer power and/or control parameters to the electronic device 100. In either event, receiver circuit components 104 internal to the electronic device 100 can capture the energy radiated by the TX antenna 1410 and convert this energy to an electrical waveform. The receiver circuit components 404 may further modify the waveform to create an electrical pulse suitable for the stimulation of neural tissue, and this pulse may be delivered to the tissue via the electrodes 108.

In some implementations, the RF pulse generator module 1406 can remotely control the stimulus parameters (that is, the parameters of the electrical pulses applied to the neural tissue) and monitor feedback from the wireless electronic device 100 based on RF signals received from the electronic device 100. A feedback detection algorithm implemented by the RF pulse generator module 1406 can monitor data sent wirelessly from the implanted electronic device 100, including information about the energy that the electronic device 100 is receiving from the RF pulse generator 1406 and information about the stimulus waveform being delivered to the electrodes 108. In order to provide an effective therapy for a given medical condition, the system can be tuned to provide the optimal amount of excitation or inhibition to the nerve fibers by electrical stimulation. A closed loop feedback control method can be used in which the output signals from the implanted electronic device 100 are monitored and used to determine the appropriate level of neural stimulation current for maintaining effective neuronal activation, or, in some cases, the patient can manually adjust the output signals in an open loop control method.

Figure 24:
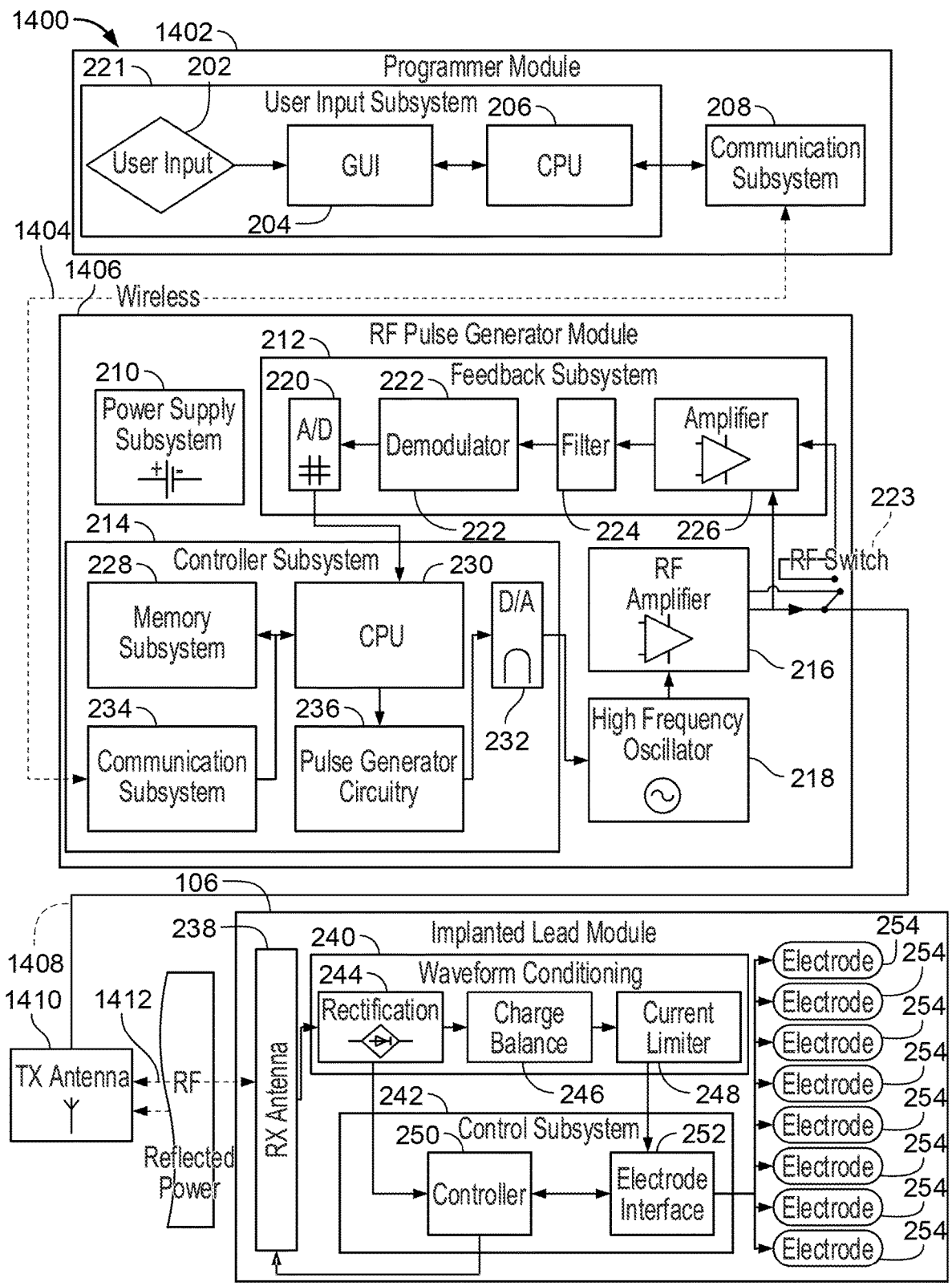
FIG. 24 is a detailed block diagram of the tissue stimulator system of FIG. 23.

FIG. 24 depicts a detailed diagram of the neural stimulation system 1400. As depicted, the programming module 1402 may comprise user input system 221 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 1404, such as Bluetooth or Wi-Fi, to the RF pulse generator module 1406, as well as receive data from module 1406.

For instance, the programmer module 1402, which can be utilized for multiple users, such as a patient's control unit or clinician's programmer unit, can be used to send stimulation parameters to the RF pulse generator module 1406. The power supply subsystem 210 can provide power for the pulse generator module 1406. The stimulation parameters that can be controlled may include pulse amplitude, pulse frequency, and pulse width in the ranges of 0 to 20 mA, 0 to 2000 Hz Pulse Width, and 0 to 2 ms, respectively. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

The electronic device 100 or RF pulse generator module 1406 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 1402 may be functionally a smart device and associated application. The smart device hardware may include a CPU 206 and be used as a vehicle to handle touchscreen input or other user input 202 on a graphical user interface (GUI) 204, for processing and storing data.

The RF pulse generator module 1406 may be connected via wired connection 1408 to an external TX antenna 1410. Alternatively, both the antenna and the RF pulse generator are located subcutaneously (not shown).

The signals sent by RF pulse generator module 1406 to the implanted stimulator 1414 may include both power and parameter-setting attributes in regards to stimulus waveform, amplitude, pulse width, and frequency. The RF pulse generator module 1406 can also function as a wireless receiving unit that receives feedback signals from the electronic device 100. To that end, the RF pulse generator module 1406 may contain microelectronics or other circuitry to handle the generation of the signals transmitted to the electronic device 100 as well as handle feedback signals, such as those from electronic device 100. For example, the RF pulse generator module 1406 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 1402 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 1406 to electronic device 100). These parameter settings can affect, for example, the power, current level, or shape of the one or more electrical pulses. The programming of the stimulation parameters can be performed using the programming module 1402, as described above, to set the repetition rate, pulse width, amplitude, and waveform that will be transmitted by RF energy to the receive (RX) antenna 238 (e.g., an embodiment of the antenna 106), typically a dipole antenna (although other types may be used), in the wireless implanted electronic device 100. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 1402. The CPU 206 may use the parameters stored in the local memory to control the pulse generator circuitry 236 to generate a stimulus waveform that is modulated by a high frequency oscillator 218 in the range from 300 MHz to 8 GHz. The resulting RF signal may then be amplified by RF amplifier 226 and then sent through an RF switch 223 to the TX antenna 1410 to reach through depths of tissue to the RX antenna 238.

In some implementations, the RF signal sent by TX antenna 1410 may simply be a power transmission signal used by electronic device 100 to generate electric pulses. In other implementations, a telemetry signal may also be transmitted to the electronic device 100 to send instructions about the various operations of the electronic device 100. The telemetry signal may be sent by the modulation of the carrier signal (through the skin if external, or through other body tissues if the pulse generator module 1406 is implanted subcutaneously). The telemetry signal is used to modulate the carrier signal (a high frequency signal) that is coupled onto the implanted antenna(s) 238 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 223 may be a multipurpose device such as a dual directional coupler, which passes the relatively high amplitude, extremely short duration RF pulse to the TX antenna 1410 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 1410, and the other output delivers a reverse power signal to a different port of the feedback subsystem 212, where reverse power is an attenuated version of the reflected RF energy from the TX Antenna 1410.

During the on-cycle time (when an RF signal is being transmitted to electronic device 100), the RF switch 223 is set to send the forward power signal to feedback subsystem. During the off-cycle time (when an RF signal is not being transmitted to the electronic device 100), the RF switch 223 can change to a receiving mode in which the reflected RF energy and/or RF signals from the electronic device 100 are received to be analyzed in the feedback subsystem 212.

The feedback subsystem 212 of the RF pulse generator module 1406 may include reception circuitry to receive and extract telemetry or other feedback signals from electronic device 100 and/or reflected RF energy from the signal sent by TX antenna 1410. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 1406. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 1410 has perfectly matched impedance to the tissue that it contacts, the electromagnetic waves generated from the RF pulse generator 1406 pass unimpeded from the TX antenna 1410 into the body tissue. However, in real-world applications a large degree of variability may exist in the body types of users, types of clothing worn, and positioning of the antenna 1410 relative to the body surface. Since the impedance of the antenna 1410 depends on the relative permittivity of the underlying tissue and any intervening materials, and also depends on the overall separation distance of the antenna from the skin, in any given application there can be an impedance mismatch at the interface of the TX antenna 1410 with the body surface. When such a mismatch occurs, the electromagnetic waves sent from the RF pulse generator 1406 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 1406. For example, for a moderate degree of reflected power the course of action can be for the controller subsystem 214 to increase the amplitude of RF power sent to the TX antenna 1410, as would be needed to compensate for slightly non-optimum but acceptable TX antenna coupling to the body. For higher ratios of reflected power, the course of action can be to prevent operation of the RF pulse generator 1406 and set a fault code to indicate that the TX antenna 1410 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 242 of the electronic device 100 may transmit informational signals, such as a telemetry signal, through the antenna 238 to communicate with the RF pulse generator module 1406 during its receive cycle. For example, the telemetry signal from the electronic device 100 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 1406. The antenna(s) 238 may be connected to electrodes 254 (e.g., embodiments of the electrodes 108) in contact with tissue to provide a return path for the transmitted signal. An A/D (not shown) converter can be used to transfer stored data to a serialized pattern that can be transmitted on the pulse modulated signal from the internal antenna(s) 238 of the neural stimulator.

A telemetry signal from the implanted wireless electronic device 100 may include stimulus parameters such as the power or the amplitude of the current that is delivered to the tissue from the electrodes. The feedback signal can be transmitted to the RF pulse generator module 1406 to indicate the strength of the stimulus at the nerve bundle by means of coupling the signal to the implanted RX antenna 238, which radiates the telemetry signal to the external (or remotely implanted) RF pulse generator module 1406. The feedback signal can include either or both an analog and digital telemetry pulse modulated carrier signal. Data such as stimulation pulse parameters and measured characteristics of stimulator performance can be stored in an internal memory device within the implanted electronic device 100, and sent on the telemetry signal. The frequency of the carrier signal may be in the range of at 300 MHz to 8 GHz.

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify that the electronic device 100 delivered the specified stimuli to tissue. For example, if the electronic device 100 reports a lower current than was specified, the power level from the RF pulse generator module 1406 can be increased so that the implanted electronic device 100 will have more available power for stimulation. The implanted electronic device 100 can generate telemetry data in real time, for example, at a rate of 8 kbits per second. All feedback data received from the implanted electronic device 100 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the electronic device 100 by the control subsystem 242 and routed to the appropriate electrodes 254 that are placed in proximity to the tissue to be stimulated. For instance, the RF signal transmitted from the RF pulse generator module 1406 may be received by RX antenna 238 and processed by circuitry, such as waveform conditioning circuitry 240, within the implanted wireless electronic device 100 to be converted into electrical pulses applied to the electrodes 254 through electrode interface 252. In some implementations, the implanted electronic device 100 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 1406. The rectifier signal may also be fed to a charge balance component 246 that is configured to create one or more electrical pulses based such that the one or more electrical pulses result in a substantially zero net charge at the one or more electrodes (that is, the pulses are charge balanced). The charge balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless electronic device 100 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 238. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 1406 can reduce the RF power delivered to the body if the implanted wireless electronic device 100 reports it is receiving excess RF power.

The controller 250 of the stimulator 1406 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 1406 has multiple electrodes 254 in contact with tissue, and for a given stimulus the RF pulse generator module 1406 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 1406) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 238, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode.

The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 1406. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the electronic device 100 may include a charge balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The electronic device 100 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless electronic device 100 may create a drive-waveform envelope that follows the envelope of the RF pulse received by the receiving dipole antenna(s) 238. In this case, the RF pulse generator module 1406 can directly control the envelope of the drive waveform within the wireless electronic device 100, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted electronic device 100 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the electronic device 100 may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 1406, and in others this control may be administered internally by circuitry onboard the electronic device 100, such as controller 250. In the case of onboard control, the amplitude and timing may be specified or modified by data commands delivered from the pulse generator module 1406.

Other embodiments of electronic devices and tissue stimulation systems are within the scope of the following claims.

What is claimed is:

1. An implantable electronic device, comprising:
a flexible circuit board;
one or more circuit components attached to the flexible circuit board and configured to convert electrical energy into electrical pulses;
one or more electrodes attached to the flexible circuit board without cables connecting the electrodes to each other or to the flexible circuit board, the one or more electrodes configured to apply the electrical pulses to a tissue adjacent the implantable electronic device; and
one or more joints that attach the one or more electrodes to the flexible circuit board.

2. The implantable electronic device of claim 1, wherein the one or more joints include a rectangular joint.

3. The implantable electronic device of claim 1, wherein the one or more joints comprise one or more of stainless steel, platinum, platinum-iridium, gallium-nitride, titanium-nitride, and iridium-oxide.

4. The implantable electronic device of claim 1, wherein the one or more joints are part of the one or more electrodes.

5. The implantable electronic device of claim 1, wherein the one or more joints have a thickness of about 0.05 mm to about 0.5 mm.

6. The implantable electronic device of claim 1, wherein the one or more electrodes are attached to the flexible circuit board respectively along one or more interior surfaces of the one or more electrodes.

7. The implantable electronic device of claim 6, wherein the one or more interior surfaces have a shape that is complimentary to at least one or more portions of one or more joints.

8. The implantable electronic device of claim 1, wherein the one or more electrodes are attached to the flexible circuit board respectively along one or more exterior surfaces of the one or more electrodes.

9. The implantable electronic device of claim 8, wherein the one or more exterior surfaces have a shape that is complimentary to at least one or more portions of one or more joints.

10. The implantable electronic device of claim 1, wherein the one or more electrodes are attached to the flexible circuit board in an automated manner.

11. The implantable electronic device of claim 1, wherein the one or more electrodes are attached to the flexible circuit board via laser welding, soldering, or conductive epoxy application.

12. The implantable electronic device of claim 1, wherein the one or more electrodes have a generally tubular shape.

13. The implantable electronic device of claim 1, wherein the one or more electrodes are directly attached to the flexible circuit board.

14. The implantable electronic device of claim 1, wherein the one or more electrodes are attached to the flexible circuit board within a compressive mechanical structure.

15. The implantable electronic device of claim 1, further comprising an antenna attached to the flexible circuit board and configured to receive an input signal carrying the electrical energy.

16. The implantable electronic device of claim 15, wherein the antenna comprises a layer of the flexible circuit board.

17. The implantable electronic device of claim 15, wherein the antenna is oriented parallel to one or more circuits.

18. The implantable electronic device of claim 15, wherein the antenna is oriented perpendicular to one or more circuits.

19. The implantable electronic device of claim 15, wherein the antenna comprises two separate portions.

20. The implantable electronic device of claim 1, wherein the implantable electronic device is sized to be passed through an introducer needle.

* * * * *